(12) United States Patent
Jackson et al.

(10) Patent No.: US 6,645,147 B1
(45) Date of Patent: Nov. 11, 2003

(54) DIAGNOSTIC MEDICAL ULTRASOUND IMAGE AND SYSTEM FOR CONTRAST AGENT IMAGING

(75) Inventors: John I. Jackson, Menlo Park, CA (US); Jay S. Plugge, Sunnyvale, CA (US); Edward A. Gardner, San Jose, CA (US)

(73) Assignee: Acuson Corporation, Mountain View, CA (US)

( * ) Notice: Subject to any disclaimer, the term of this patent is extended or adjusted under 35 U.S.C. 154(b) by 0 days.

(21) Appl. No.: 09/200,648

(22) Filed: Nov. 25, 1998

(51) Int. Cl.$^7$ .................................................. A61B 8/00
(52) U.S. Cl. ..................................................... 600/458
(58) Field of Search ................................ 600/458, 443, 600/444, 454, 462, 460, 459; 382/294, 295

(56) References Cited

U.S. PATENT DOCUMENTS

| | | | |
|---|---|---|---|
| 3,938,502 A | | 2/1976 | Bom |
| 4,917,097 A | | 4/1990 | Proudian et al. |
| 5,285,788 A | | 2/1994 | Arenson et al. |
| 5,297,553 A | | 3/1994 | Sliwa, Jr. et al. |
| 5,345,940 A | | 9/1994 | Seward et al. |
| 5,456,257 A | * | 10/1995 | Johnson et al. ............ 600/458 |
| 5,549,111 A | | 8/1996 | Wright et al. |
| 5,551,433 A | | 9/1996 | Wright et al. |
| 5,555,534 A | | 9/1996 | Maslak et al. |
| 5,570,691 A | | 11/1996 | Wright et al. |
| 5,577,505 A | | 11/1996 | Brock-Fisher et al. |
| 5,581,517 A | | 12/1996 | Gee et al. |
| 5,617,862 A | | 4/1997 | Cole et al. |
| 5,623,928 A | | 4/1997 | Wright et al. |
| 5,632,277 A | | 5/1997 | Chapman et al. |
| 5,667,373 A | | 9/1997 | Wright et al. |
| 5,699,805 A | | 12/1997 | Seward et al. |
| 5,713,363 A | | 2/1998 | Seward et al. |
| 5,738,100 A | * | 4/1998 | Yagami et al. .............. 600/459 |
| 5,740,808 A | | 4/1998 | Panescu et al. |
| 5,741,522 A | | 4/1998 | Violante et al. |
| 5,793,701 A | | 8/1998 | Wright et al. |
| 5,795,299 A | | 8/1998 | Eaton et al. |
| 5,797,848 A | | 8/1998 | Marian et al. |

(List continued on next page.)

FOREIGN PATENT DOCUMENTS

EP 0 700 352 A1 5/1997

OTHER PUBLICATIONS

Richard E. Kerber, MD, *Coronary Risk Areas: Measurements by Intracardiac Echo and Ultrasound Contrast*, Sep., 1998, p. 8.

James B. Seward et al, *Mayo Clinic Proceedings Ultrasound Cardioscopy: Embarking on a New Journey*, Jul., 1996, vol. 71, No. 7, pp. 629–635.

*Primary Examiner*—Marvin M. Lateef
*Assistant Examiner*—Maulin Patel

(57) ABSTRACT

A method and system for contrast agent imaging with a catheter transducer is provided. The catheter transducer may comprise an intra-vascular, intra-cardiac or other transducer for insertion into or through a small space. The catheter transducer is inserted within the heart or other portion of a patient. Contrast agents, such as micro-spheres, are injected into the patient. Using the catheter transducer, ultrasonic acoustic energy is transmitted, and reflected energy is received. The reflected energy is responsive to the contrast agents. An image processor generates an image of the tissue and contrast agents as a function of the reflected energy. The image provides an indication of perfusion. Alternatively, the ultrasound system calculates perfusion. By generating intra-vascular images or data, interference from other tissues is avoided. Therefore, the perfusion information obtained may have higher resolution. Images with better resolution better assist doctors in medical diagnosis.

53 Claims, 5 Drawing Sheets

U.S. PATENT DOCUMENTS

| | | |
|---|---|---|
| 5,808,962 A | 9/1998 | Steinberg et al. |
| 5,823,962 A | 10/1998 | Schaetzle et al. |
| 5,833,613 A | 11/1998 | Averkiou et al. |
| 5,833,615 A | 11/1998 | Wu et al. |
| 5,846,205 A * | 12/1998 | Curley et al. ............... 600/463 |
| 5,885,218 A * | 3/1999 | Teo et al. ................... 600/443 |
| 6,201,900 B1 * | 3/2001 | Hossack et al. ............ 382/294 |

* cited by examiner

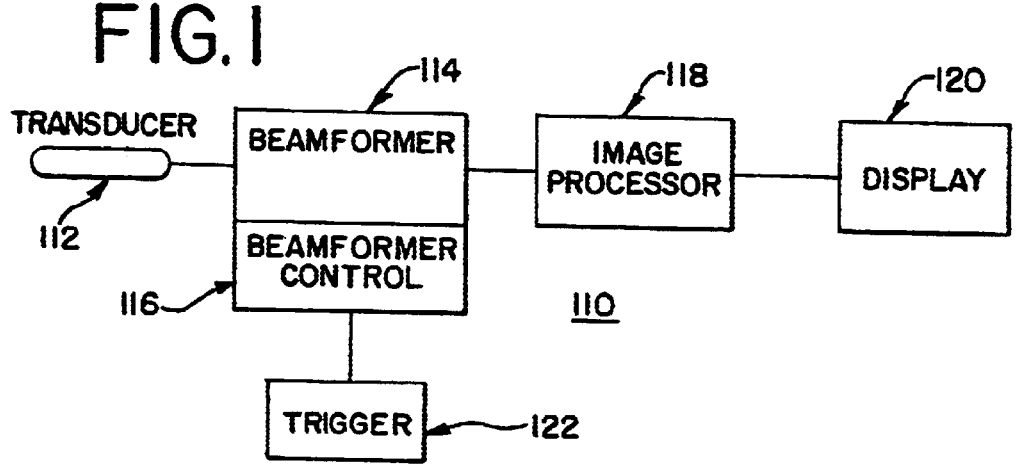
FIG. 1
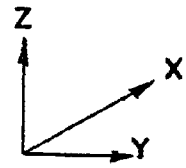
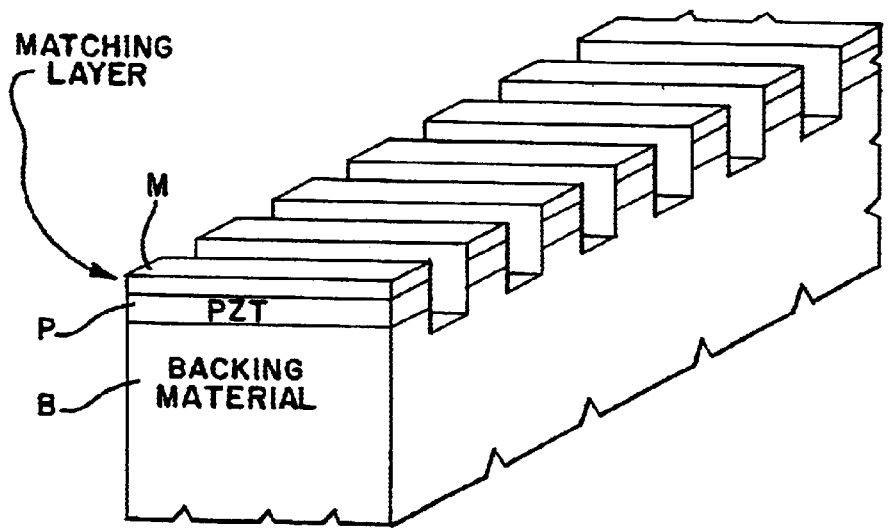
FIG. 2

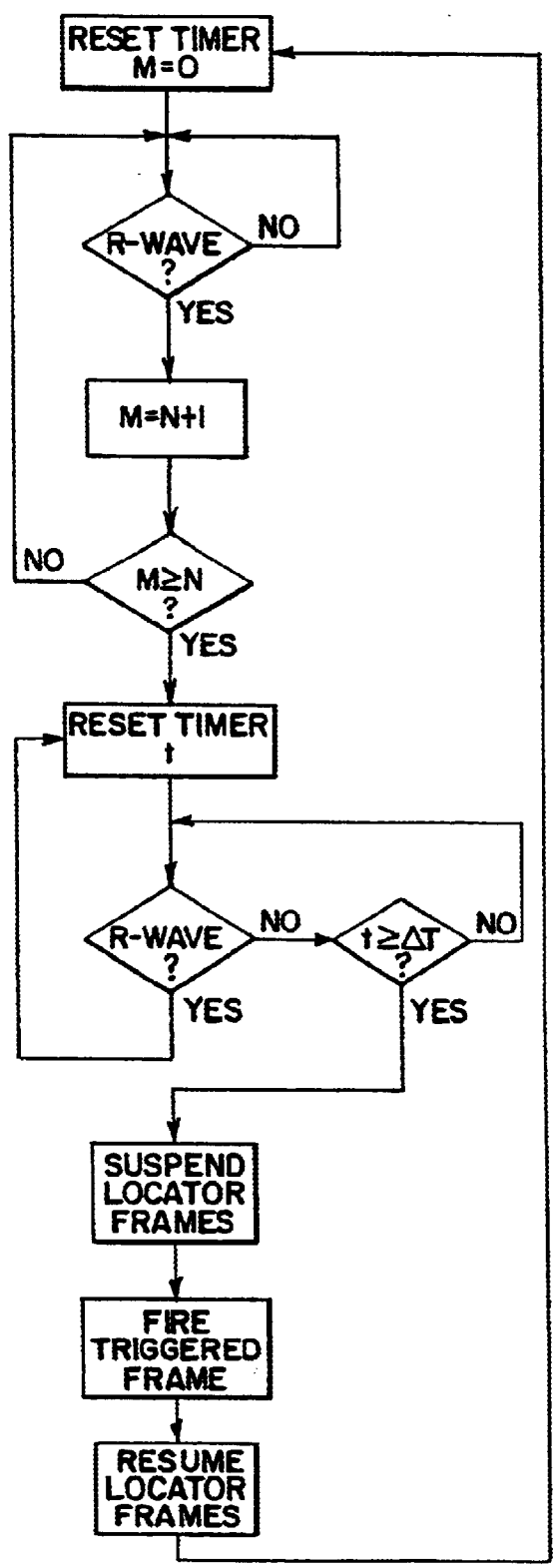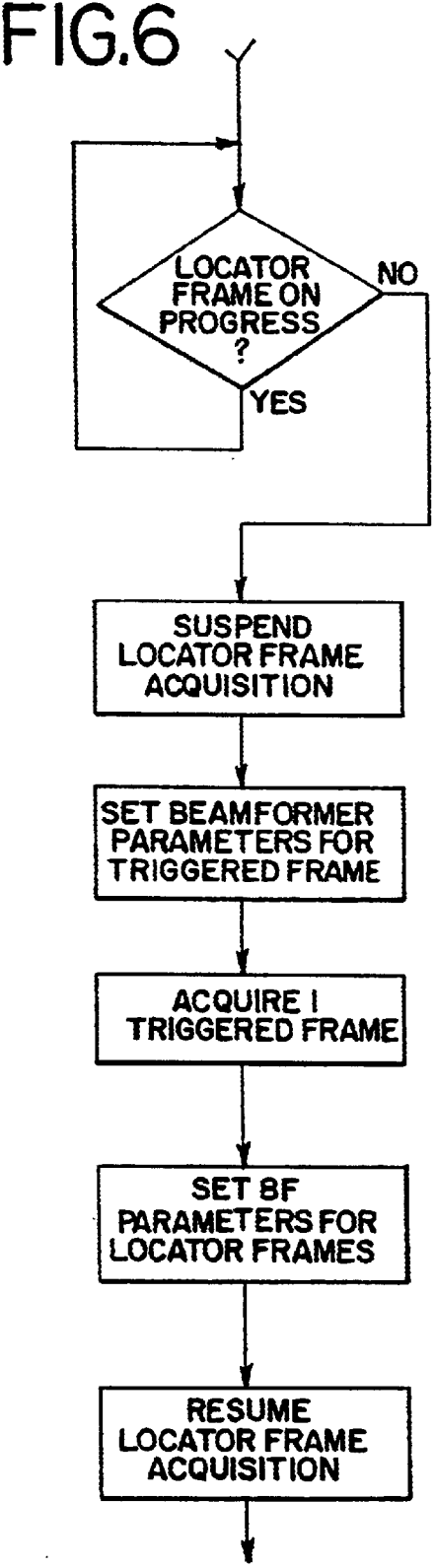

DIAGNOSTIC MEDICAL ULTRASOUND IMAGE AND SYSTEM FOR CONTRAST AGENT IMAGING

BACKGROUND OF THE INVENTION

This invention relates to an ultrasound system and method for medical imaging, and in particular, for assisting in medical diagnosis using a catheter transducer.

Catheter transducers include catheter mounted transducer arrays. Catheter-mounted ultrasonic transducers have in the past taken several forms, including (1) single-element transducer crystals that are pointed radially outward and rotated about the axis of the catheter, (2) radial array transducers, and (3) linear array transducers. Bom U.S. Pat. No. 3,958, 502 discloses one catheter-mounted ultrasonic array which utilizes a radial array arranged circumferentially around the axis of the catheter. Proudian U.S. Pat. No. 4,917,097 describes a similar radial array (and alludes to other geometries) that require multiplexing of the ultrasound signals near the elements of the array. Seward et al. (Seward, J. B., D. L. Packer, R. C. Chan, M. G. Curley, A. J. Tajik (1996), "Ultrasound Cardioscopy: Embarking on a New Journey," *Mayo Clinic Proceedings*, 71(7)) have described a phased array transducer for insertion into the heart. Such an array has the advantage of increased power: as the transducer array is made longer, the number of elements can be increased, thereby increasing the total radiation area.

Catheter transducer include intra-cardiac and intra-vascular transducers Intra-cardiac transducers are used to image tissue from inside a chamber of the heart. Intra-vascular transducers are used to image tissue from inside a vessel. Catheter transducers provide images of particular tissue with minimal interference from transmission and reception through multiple layers of other tissue.

Ultrasound imaging through multiple layers of tissue (e.g. by a transducer placed adjacent the skin of a patient) has been used to assess the health of tissue within the body. Methods that may be used for this assessment include Doppler based methods, such as Doppler imaging of tissue. In this method, Doppler based processing is used to measure the velocity of tissue within a region being examined. Knowledge of tissue movement, especially in relation to the motion of the neighboring regions, can indicate tissue health.

Perfusion measurements also provide diagnostic information. Perfusion is the blood flow per unit of tissue mass that supplies the tissue with oxygen and nutrients (volume/(time*mass)). Ultrasound systems may also be used to estimate perfusion. Methods for estimating perfusion include measuring the wash in and wash out times of contrast agents injected into the blood stream at a region of interest as the contrast agent enters and exits the region of interest.

BRIEF SUMMARY

The present invention is defined by the following claims, and nothing in this section should be taken as a limitation on those claims. By way of introduction, the preferred embodiment described below includes a method and system for contrast agent imaging with a catheter transducer. As used herein, the catheter transducer includes intra-vascular, intra-cardiac or transducers for insertion into small spaces, such as the urinary tract. The catheter transducer is inserted within the heart or other portion of a patient. Contrast agents, such as micro-spheres, are injected into the patient. Using the catheter transducer, ultrasonic acoustic energy is transmitted, and reflected energy is received. The reflected energy is responsive to the contrast agents. An image processor generates an image of the tissue and contrast agents as a function of the reflected energy.

The image provides an indication of perfusion. Alternatively, the ultrasound system calculates perfusion. By generating intra-vascular images or data, interference from other tissues is avoided. Therefore, the perfusion information obtained may have higher resolution. Images with better resolution better assist doctors in medical diagnosis.

Further aspects and advantages of the invention are discussed below in conjunction with the preferred embodiments.

BRIEF DESCRIPTION OF SEVERAL VIEWS OF THE DRAWINGS

FIG. 1 is a block diagram of an ultrasound system for imaging with a catheter transducer.

FIG. 2 is a schematic perspective view of a phased-arrayed ultrasonic transducer.

FIG. 5 is a flow chart illustrating operation of the beamformer controller of FIG. 1.

FIG. 6 is a flow chart providing further details regarding operation of the beamformer controller of FIG. 1.

DETAILED DESCRIPTION OF THE INVENTION

Figure 4:
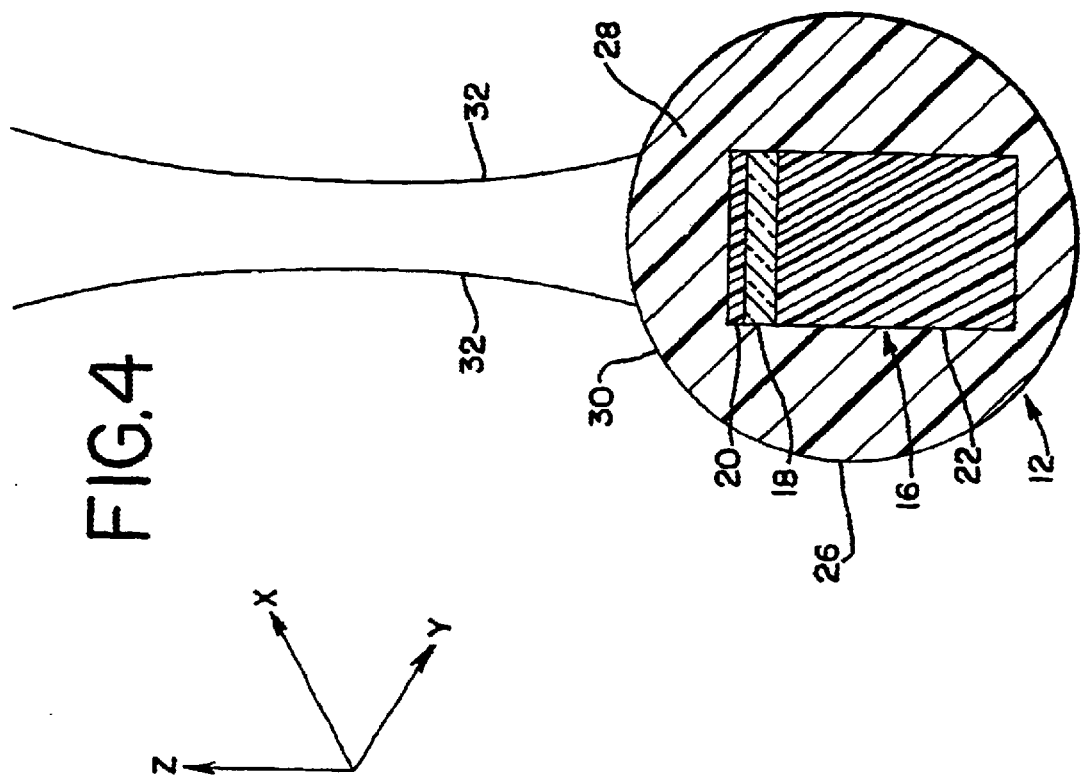
FIG. 4 is a cross-sectional view of the catheter mounted transducer of FIG. 3.

Imaging from within the body allows for higher resolution images of structure in the body. For example, imaging with a catheter transducer in the heart provides images of the myocardium without interference from the lungs, ribs or even other tissue layers. Many cardiac structures may be more uniformly imaged from within the heart than from outside the heart. A catheter transducer positioned in the left ventrical of the heart may provide images of each side of the left ventrical with minimal interference. Cardiac structures and motion may be clearly visualized with B-mode imaging or may be aided by Doppler imaging of tissue. Further advantages are provided by injecting contrast agents with any device and imaging the contrast agents with the catheter transducer. Through selective injection into one or more of the major coronary arteries, perfusion is observed from images with minimized interference. Perfusion information may be used for medical diagnosis. By providing accurate perfusion information and/or tissue information, the catheter transducer may be used to assess the benefits and to guide any intervention, such as angioplasty, atherectomy, stent placement or transmyocardial revascularization.

Referring to FIG. 1, an ultrasound system for imaging contrast agents with a catheter transducer is shown at 110. The ultrasound system 110 includes a catheter transducer 112, a beamformer 114, a beamformer controller 116, an image processor 118, a display 120 and a trigger source 122. Other systems, such as systems not including the trigger source 122, may be used. The various elements of FIG. 1 may be formed in any suitable manner, including a wide variety of conventional systems. The widest variety of triggers, beamformer controllers, beamformers, intravascular transducers, image processors and displays may be adapted for use with this invention. Both analog and digital beamformer systems are suitable, and a wide variety of signals can be provided as inputs to the trigger source 122. By way of example, without intending any limitation, the ultrasound imaging systems marketed by Acuson Corporation under the trade names Sequoia® and Aspen™ are capable of being modified to implement this invention. The Sequoia ultrasound imaging system is described for example in the following patents, assigned to the assignee of the present invention:

U.S. Pat. Nos. 5,549,111, 5,551,433, 5,555,534, 5,570, 691, 5,581,517, 5,617,862.

A. Catheter Transducer

The catheter transducer 112 comprises any one of various transducers for insertion into the vascular system of a patient, such as single element transducers, radial array transducers or linear array transducers. For example, the catheter transducers described by Seward, et al. ("Ultrasound Cardioscopy: Embarking on a New Journey," *Mayo Clinic Proceedings*, 71(7)(1996); and U.S. Pat. Nos. 5,713,363 and 5,345,940) are used. Seward et al. describe a phased array ultrasound transducer for insertion into the heart. This transducer utilizes a linear phased array of the type shown in FIG. 2, and it offers many improvements over catheter-based radial imaging transducers of the past. These advantages are detailed in the Seward paper, but can be briefly listed as follows: the image plane is advantageous when imaging therapeutic interventions in the heart; the overall aperture of the transducer is large, improving the ultrasound energy and the penetration depth of the tissue; and the transducer is compatible with modem ultrasonic scanning systems. The linear array may be used for imaging in linear, sector, Vector®, or other formats The Seward transducer is made of conventional materials, including an epoxy-based backing block and a silicone-based lens. The transducer is constructed of 128 elements operating at 5 or 7 MHz. The total array extends for 14 mm in the X direction and 3.3 mm in the Y direction. The backing block is 5 mm in depth or more. As such, the overall diameter of this catheter is 8 mm. If the lens were formed into a cylinder with an 8 mm diameter, it would cause the ultrasound focus to be too close to the transducer, and the ultrasound field would then begin to diverge quickly, causing a loss of image quality and a loss of sensitivity and penetration depth. For this reason, the lens of the Seward transducer is flattened in the region of the transducer, making the forming of the final catheter more difficult.

Figure 3:
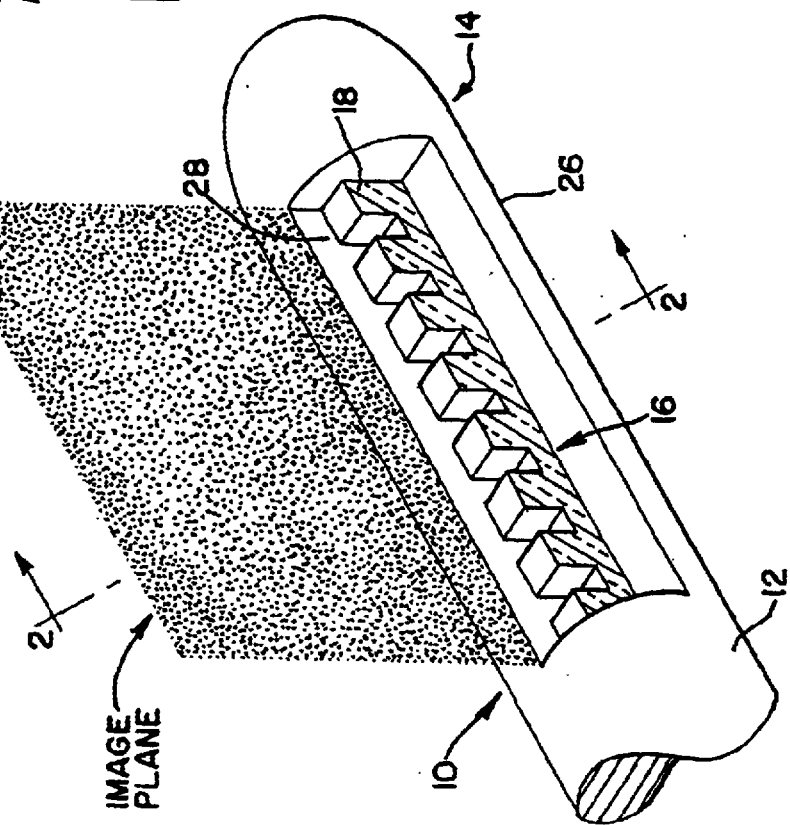
FIG. 3 is a perspective view in partial cutaway of a portion of a catheter-mounted transducer that incorporates a presently preferred embodiment of this invention.

FIG. 3 shows a perspective view of a intra-vascular transducer assembly 10 that incorporates a presently preferred embodiment of the intravascular transducer 112. This transducer is described in U.S. Pat. No. 5,846,205 (U.S. Application Ser. No. 08/791,598 filed Jan. 31, 1997), assigned to Acuson Corporation, the disclosure of which is incorporated herein by reference. The transducer assembly 10 includes a catheter 12 which defines a distal end 14. In this embodiment the proximal end (not shown) is spaced from the distal end by about 110 centimeters, and the catheter 12 is circular in cross section and defines a maximum cross-sectional dimension of about 3.3 mm.

The distal end 14 of the catheter 12 carries a linear array 16 of transducer elements 18. The transducer elements 18 define an azimuthal axis which is denominated the X axis in FIG. 3, and is parallel to the longitudinal axis of the catheter 12.

As shown in FIG. 4, the transducer array 16 includes a matching layer 20 adjacent the active surface of the transducer elements 18, and a backing layer 22 on the reverse side of the transducer elements 18. Flexible circuits are disposed in a lumen defined by the catheter 12 to carry transmit signals and receive signals between the individual transducer elements 18 and an ultrasonic diagnostic imaging system (not shown).

As shown in FIGS. 3 and 4, the catheter 12 includes an end portion 26 that is secured to the tube of the catheter 12 and surrounds the transducer array 16. The part of the end portion 26 that overlies the active surface of the transducer elements 18 forms an acoustic window 28. Typically, the end portion 26 and the acoustic window 28 may be formed of the same material, though this is not required. In this embodiment the end portion 26 is circular in cross section, and the radially outer surface 30 of the acoustic window 28 defines a radius of curvature which is substantially equal to one-half of the maximum cross-sectional dimension of the end portion 26. Since the end portion 26 is circular in cross section in this embodiment, the radius of curvature of the surface 30 is equal to the radius of curvature of the remaining parts of the end portion 26. This arrangement simplifies fabrication of the transducer assembly 10, because it eliminates both the need for a complex shape for the window, and the need for accurate registration between the transducer and the window.

Preferably the maximum cross-sectional dimension of the end portion 26 and the catheter 12 is less than 8 mm. This dimension is more preferably less than 3.3 mm, and most preferably less than 2 mm.

The acoustic window 28 is formed of a material that propagates ultrasonic waves at a speed comparable to or greater than the speed at which such ultrasonic waves propagate in adjacent tissue such as blood. As is known in the art, the propagation speed of ultrasound energy in blood is about 1570 meters per second, and the acoustic window 28 is preferably formed of a material having a comparable speed of sound for ultrasonic energy. The speed of sound in the window 28 is preferably greater than about 1250 m/sec. (1570 m/sec-20%), more preferably greater than about 1410 m/sec (1570 m/sec-10%), and most preferably greater than or equal to about 1570 m/sec. As used herein, the term "acoustic window" is intended to encompass both non-focusing and de-focusing elements between the active surface of the array and the tissue being scanned.

When the acoustic window 28 provides a speed of sound comparable to that of adjacent tissue, the radius of curvature of the radially outer surface 30 will not affect the focusing characteristics of the transducer array 16. In contrast, if conventional materials were used for the acoustic window 28 and the radius of curvature of the radially outer surface 30 were maintained at 1.5 millimeters (3 mm diameter for the end portion 26), the result would be an ultrasonic focus located too close to the transducer array 16. Such a close focus would cause the ultrasonic field to diverge rapidly at depths greater than the focal region, causing poor image quality and a loss of imaging depth.

However, it may be desirable to increase the thickness in the Y dimension if the natural thickness when the field is unfocussed is too thin. If the field is too thin, then objects would appear, then disappear from the image if the catheter, hence the ultrasound field, were rotated slightly. If the speed of sound in the material surrounding the transducer were greater than in the surrounding blood, and this material were convex, then the ultrasound field would diverge upon exiting the catheter. This would increase the thickness of the field in the Y dimension, which would have desirable properties for keeping objects in the image field with slight rotation of the transducer.

The design of the ultrasound imaging field may be different for different applications. When the image field needs to be wide, then a material with a speed of sound faster than that of blood can be used. When it is desirable to keep the image width narrow, and with minimal variation in the thickness of the image field, then a material with a speed of sound close to that of blood can be used.

In FIG. 4, lines 32 schematically show the ultrasonic field boundaries for the situation where the acoustic window 28 is formed of a material having a speed of sound close to that of tissue. If this material also has an acoustic impedance close to that of tissue, the ultrasound field generated by the transducer array 16 propagates as if it is simply contacting the tissue, and there is no significant reflection of the ultrasonic field as it exits the acoustic window 28. Similarly, there is no significant reflection of ultrasonic energy at this interface because of the substantially identical acoustic impedance on both sides of the surface 30.

Preferably, the length of each transducer element 18 in the Y direction is larger than a wavelength of ultrasonic energy, and the material of the acoustic window 28 is selected as described above. In this case the transducer array 16 will exhibit a gentle, natural focus. The distance in the Z dimension from the transducer array 16 to the location at which the thickness of the ultrasonic field in the Y dimension is smallest is approximately equal to $$FocalDepth = \frac{l^2 f}{2c},$$

where c is the speed of sound in tissue (1570 m/sec), l is the elevational length of the transducer elements 18, and f is the ultrasound frequency. When the transducer 16 measures 2.5 mm in the Y dimension and operates at 7 MHz in a 3.3 mm diameter catheter having an acoustic window as described above, the point of best focus is approximately 14 mm away from the transducer array 16. Beyond this depth the ultrasound field gradually diverges in the Y dimension.

The use of non-focusing material for the acoustic window 28 both improves the imaging characteristics of the transducer array 16 and simplifies manufacture of the acoustic window 28. In particular, the acoustic window 28 can be formed with a simple cylindrical shape, and in this way the need for compound curvatures in the region of the transducer is completely avoided, along with the need for precise registration between the transducer and the compound curvatures.

In order better to define the presently preferred embodiments of this invention, the following details of construction are provided. It should be understood that these details are intended only by way of example.

The backing layer 22 may be formed as described in Sliwa U.S. Pat. No. 5,297,933, assigned to Acuson Corporation. The backing material disclosed in the Sliwa patent provides excellent acoustic properties while allowing the matching layer 20 and therefore the catheter 12 to be provided with an extremely low profile. The end portion 26 may be formed of urethane (for example the resin CY8721 sold by Ciba-Geigy) or polyether block Amides (for example the resin Pebax sold by Autochem). Urethane may be used as an adhesive to secure the Pebax end portion to the catheter.

Preferably, flexible circuits as described in U.S. Pat. No. 5,795,299, assigned to the assignee of the present invention, can be used in the catheter 12. If desired, the catheter 12 can be made disposable, and the inter connection system described in U.S. Pat. No. 5,797,848, also assigned to the assignee of the present invention, can be used. The entire specifications of both of these U.S. patents are incorporated herein by reference.

Referring to FIG. 3, the transducer elements 18 may be spaced apart so that each of the transducer elements 18 is spaced at least one wavelength from adjacent transducer elements 18. Using this spacing may generate grating lobes, but imaging at harmonic frequencies as discussed below reduces or eliminates the effect of the grating lobes. Harmonic imaging may also improve the effective elevation beam width. Using spaced transducer elements 18, fewer elements are needed for imaging. With fewer elements, fewer traces or inter-connects are needed. Therefore, the transducer array 16 may be used in even smaller catheters, such as catheters for placement in and imaging of the left ventricle of the heart.

Images from outside the heart are susceptible to image degradation, such as from non-uniform alignment of the muscle fibers relative to the transducer, from non-uniform wall thickness relative to the transducer, or from intervening structures. Images from within the left ventricle may reduce the amount of this image degradation. Imaging from within the heart, in particular the left ventricle, may provide more complete images of the muscle fibers. Images generated from within the heart or left ventricle provide more detail due to a better signal to noise ratio than from images from outside the heart or left ventricle. Additionally, spaced transducer elements 18 may be used for fundamental imaging, such as Doppler velocity, variance or energy or spectral Doppler. Doppler imaging typically uses low fundamental frequencies that are less susceptible to the grating lobes.

B. Ultrasound System

Referring to FIG. 1, the catheter transducer 112 operatively connects to the beamformer 114. Preferably, the beamformer comprises a programmable transmit/receive beamformer 114. The beamformer 114 provides transmit waveforms to the catheter transducer 112 which cause the catheter transducer 112 to transmit ultrasonic acoustic energy into a tissue T, optionally containing a contrast agent C. Scattering sites within the tissue T, including any contrast agent C, return reflected ultrasonic energy to the catheter transducer 112, which transmits receive waveforms to the beamformer 114. The region from which receive waveforms are collected will be referred to as the imaged region, and may include tissue, blood, and optionally contrast agent.

The beamformer controller 116 controls operation of the beamformer 114 by controlling beamformer parameters such as transmit center frequency and bandwidth, receive center frequency and bandwidth, transmit power, receive gain, and transmit line spacing. Preferably, little or no energy is transmitted at harmonics of the transmit waveforms, such as by generating a Gaussian modulated sinc wave pulse. The transmit waveform may also be pre-distorted to account for propagation effects so that the transmit waveform obtains the desired shape (i.e. limited second harmonic information) at the focal point. The beamformer controller 116 is responsive to user controls and to the trigger source 122.

The trigger source 122 is responsive to an ECG signal supplied by an ECG device, and the trigger source 122 preferably includes conventional software or hardware which recognizes the R-wave of an ECG signal and generates a trigger signal when each R-wave occurs. Various alternatives to ECG R-wave detection are possible: triggering can be based on a different feature of an ECG signal; an externally provided trigger signal; some other physiological measured signal such as respiration; or on a combination of signals (such as triggering on the first R-wave after the peak of a measured respiration signal, so as to compensate for breathing). The trigger signal is used as discussed below by the beamformer controller 116 to select appropriate beamformer parameters and/or to control timing of transmissions. For example, the trigger is used to detect contrast agent or to estimate perfusion.

Detected, formed receive beams from the beamformer 114 are sent to the image processor 118. In one embodiment, the image processor 118 includes a B-mode processing path connected in parallel with a Doppler processing path. Alternatively, only one of the B-mode or Doppler processing paths are provided. The B-mode processing path includes a detector and log compressor, and the Doppler processing path includes a quadrature demodulator, digital to analog converter and an autocovariance and moment calculator. Other implementations of B-mode and/or Doppler processing may be used. The B-mode processing path provides intensity information for imaging and for perfusion estimation, and the Doppler processing path provides velocity, variance or energy information for imaging and for tissue motion information.

For B-mode processing, the signals are detected and log compressed in the detector and log compressor. The resulting information may be stored in an acoustic buffer.

For Doppler or tissue motion processing, the demodulated and filtered signal is provided to the quadrature demodulator. The quadrature demodulator demodulates and low pass filters the information. The analog to digital converter converts the analog information to digital samples. The digital samples are filtered to obtain information associated with desired motion (e.g., fluid or tissue motion). For example, a user is able to select from different filters, each with different values of low velocity cut-off. Signals from non-moving tissue and slowly moving blood are removed from the information to isolate motion. The autocovariance and moment calculator determines the autocovariance coefficients $R(0)$, $R_0(0)$, $R_1(0)$ of the filtered samples. From these coefficients, the mean velocity, variance and energy of the Doppler information is found. Other Doppler processing paths may be used, such as fully digital, fully analog or cross-correlation (i.e. one or two-dimensional displacement as a function of multiple target interrogations) processing paths. Furthermore, velocity may be estimated as disclosed in U.S. Pat. No. 5,285,788.

After an entire scan of a region or a frame of data is acquired, the Doppler or B-mode information is provided to a scan converter for generating images for display on the display 120. The scan converter preserves the spatial orientation of the information. The image processor 118 may also include a Cine memory which stores frames of data for later playback. Other processing paths including different, additional or fewer components may be used.

The image processor 118 may also include a control processor for controlling the timing and transfer of data between and through the various processing paths discussed above. The control of the system is responsive to information from a user interface. Preferably, the user configures the ultrasound system 110 for intra-vascular imaging. The ultrasound system 110 is capable of estimating perfusion and estimating tissue motion using reflected energy received with the catheter transducer 112. Estimation of perfusion and estimation of tissue motion may aid in medical diagnosis, and intra-vascular transducer based imaging may further enhance the information for the diagnosis.

C. Processing

Contrast agents are preferably injected into the vascular system of the patient for imaging with the catheter transducer 112. Any of various methods may be used to injection the contrast agent, such as through an IV or directly into one or more coronary arteries. Contrast agents are injected into the bloodstream to increase the brightness, such as associated with B-mode intensity, of blood and blood-perfused tissues. Contrast agents may be designed to provide a brighter response at different frequencies. For example, contrast agents with a good harmonic response are injected into the blood stream.

In one embodiment, the user may configure the ultrasound system 110 for harmonic or fundamental frequency imaging, such as obtaining the B-mode information from harmonic echo information and the Doppler tissue motion information from fundamental echo information. The image processor 118 filters using bandpass filtering or demodulation techniques to isolate information at the fundamental or a harmonic of the transmit frequency. As used herein, "harmonic" is intended broadly to include sub-harmonics and fractional harmonic energy (e.g. ½ or 3⁄2 of the fundamental frequency at which the transmit beam is centered) as well as higher harmonics (e.g. 2 or 3 times the fundamental frequency at which the transmit beam is centered).

Alternative techniques for isolating harmonic information may be used. For example, multiple transmissions of acoustic energy and associated lines or frames of data are combined to generate harmonic information. A method using processing, such as subtraction, to combine scan lines is disclosed by Johnson in U.S. Pat. No. 5,456,257 and Brock-Fisher in U.S. Pat. No. 5,577,505.

Another alternative includes transmitting acoustic energy with different polarities, such as disclosed in U.S. Pat. No. 5,632,277. Acoustic energy is transmitted at a first polarity or phase. Harmonic reflection from tissue or contrast agents distorts the received reflected energy. Acoustic energy with a phase shift different than and relative to the first phase is then transmitted along substantially the same scan line. For example, a phase shift that is 180 degrees out of phase with the first phase is used. Harmonic reflection from tissue or contrast agents distorts this second received reflected energy waveform. The two reflected energy waveforms are combined by addition. The opposite polarity of the fundamental between the two waveforms cancels, and the harmonic response sums. Therefore, harmonic information is isolated. Other relative phase shifts and functions for combination may be used.

Any of the various methods of transmission as discussed above may be performed at different power levels. For example, transmissions associated with imaging to determine tissue motions, such as Doppler imaging with appropriate filtering or B-mode imaging over a period of time, may be low power transmissions.

The power is selected so that the ultrasonic waves do not destroy any contrast agent. Typically, contrast agents (which are typically composed of stabilized gas microbubbles a few microns in diameter) are fragile and easily degraded (destroyed or altered) by the ultrasound acoustic pulses used to image them. A first ultrasound frame may show the contrast agent well, but subsequent frames often show less and less signal as the contrast agent is destroyed.

Ultrasonic waves associated with B-mode harmonic imaging are also preferably associated with low power, so as not to destroy any contrast agent. In alternative embodiments, either one or both of Doppler or B-mode imaging are associated with higher power transmission (e.g. contrast agent destructive power levels).

Other combinations of power level and imaging mode may be used with various triggers. For example, acquisition of B-mode data associated with high powered transmission may be triggered, and acquisition of Doppler data associated with lower power transmissions may be continuous. The ultrasound system 110 may also operate without triggering regardless of transmission power levels.

A flow chart illustrating one mode of operation of the beamformer controller 116 of FIG. 1 for triggered imaging using different transmit parameters is given as FIG. 5. In this mode, the user selects a count of R-waves N and a programmable trigger delay ΔT. A counter M is initially set to 0. The controller 16 counts R-waves until N R-waves have been detected, then initializes a timer t. When the programmed interval ΔT elapses without interruption by an R-wave, the controller suspends acquisition of any further low power transmit frames (herein "locator frames") after completion of any frame acquisition in progress. After locator frame acquisition has been completed, the controller changes beamformer parameters (e.g., setting the transmit power to maximum and selecting a fundamental or harmonic receive center frequency), and acquires a single triggered frame. Following acquisition of the triggered frame, the controller changes beamformer parameters again (reducing the transmit power and selecting a harmonic or fundamental receive center frequency) and resumes continuous firing of locator frames. The process then begins anew. The latter three steps of suspending locator frame acquisition, acquiring a triggered frame, and resuming locator frame acquisition are shown in more detail in FIG. 6.

Figure 7:
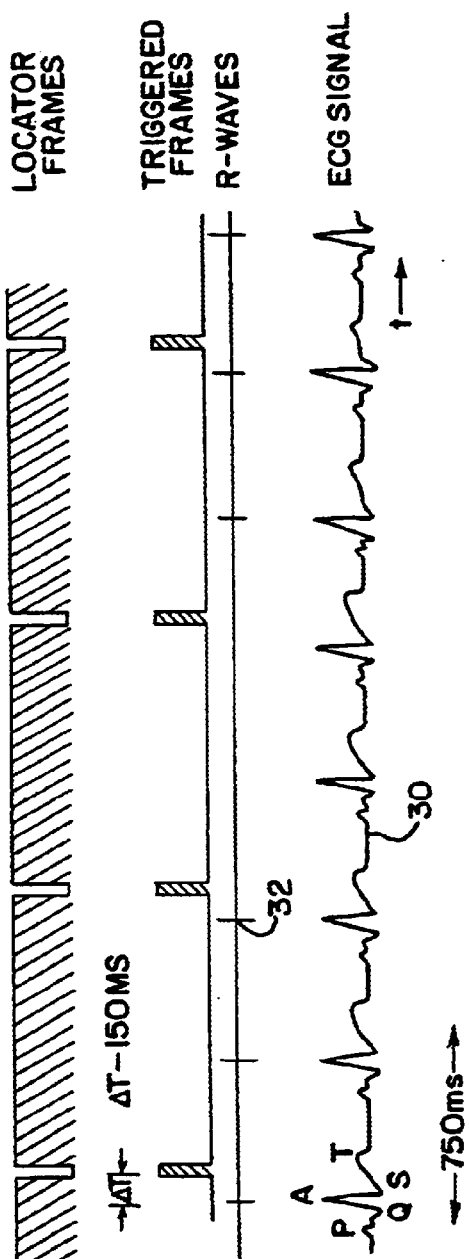
FIG. 7 is a timing diagram illustrating a first mode of operation of the imaging system of FIG. 1.

The operation of the ultrasound system 110 of FIG. 1 is illustrated schematically in FIG. 7. An ECG waveform is shown across the bottom of the figure. Within the trigger source 122, conventional software or circuitry detects the peak of the R-wave, as illustrated by the vertical lines above the ECG waveform. In this example, the interval between R-waves is 750 ms (heart rate=80 bpm) and the trigger source 122 generates a trigger signal 150 ms after every second R-wave (N=2, ΔT=150 ms). At each trigger, acquisition of locator 10 frames is suspended, and a single triggered frame is acquired using alternate beamforming parameters such as those suggested above (harmonic imaging; high transmit power). Following acquisition of the triggered frame, acquisition of locator frames resumes using the appropriate beamformer parameters (fundamental imaging; low transmit power).

In this implementation, both locator frames and imaging frames (triggered frames) are directed to the screen as they are acquired, forming an apparently continuous image (with a flicker as each triggered frame is acquired). On later Cine review, the triggered frames may be distinguished from the locator frames. Alternately, locator frames may be excluded from later cine review. Additionally the locator and image frames may be combined (optionally color-coding one image then adding the two together) into a single image. The user would then see a superposition of a relatively static image (the triggered frames) with a more dynamic one (the locator frames).

In addition to changing transmit power and selecting fundamental vs. harmonic imaging, the transmit center frequency, spectral shape, and/or bandwidth can be different for the locator and triggered frames. Contrast agents increase sound scattering through a resonance phenomenon, and the center frequency of that resonance varies inversely with bubble size. Bubbles of a given size scatter more energy (and may produce higher levels of harmonics) at or near the corresponding resonance frequency. At the same time, bubbles are more likely to be destroyed by ultrasound at or near their resonance frequency than by ultrasound away from their resonance frequency. Contrast agents achieve a broad bandwidth of contrast enhancement partly because each agent as injected includes many bubbles of different sizes and hence different resonance frequencies.

Figure 8A:
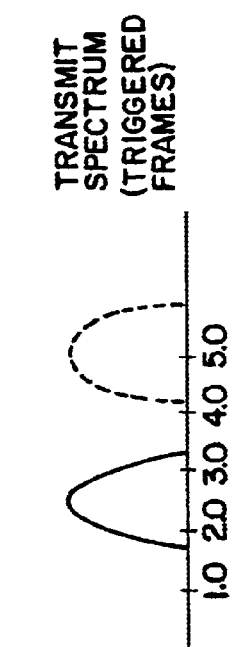
FIGS. 8A and 8B are frequency diagrams of transmit and receive spectral for modes of operation of the ultrasound system of FIG. 1.
Figure 8B:
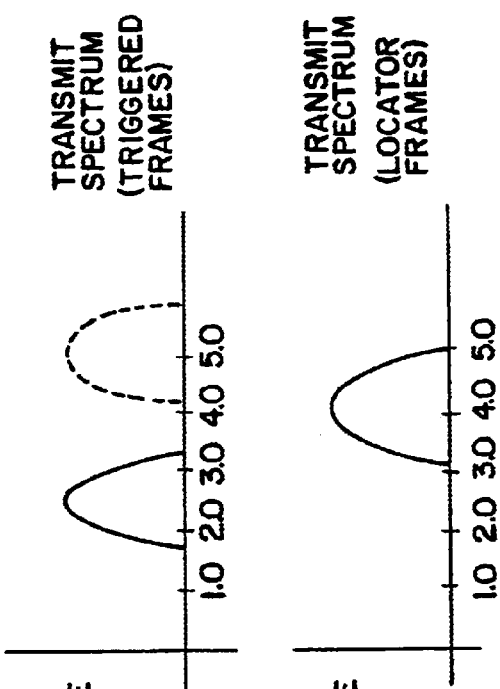

FIGS. 8A–8D show how these properties of contrast agents may be used advantageously to reduce bubble destruction. FIG. 8A shows one preferred transmit spectrum for the triggered frames, centered at 2.5 MHz. The triggered frames may be acquired in fundamental or harmonic imaging (in which case the receive spectrum would be as shown by the dashed line curve); in either case, the greatest contribution to the image comes from bubbles with resonance near 2.5 MHz. FIG. 8B shows a preferred transmit spectrum of locator frames, centered (for example) at 4.0 MHz. While the locator frames may be optimized to minimize bubble destruction, some bubbles may be destroyed anyway. However, the destroyed bubbles will tend to have a resonance frequency at or near 4.0 MHz. The bubbles destroyed by the locator frames are not those bubbles primarily imaged by the triggered frames. Additional benefit may be derived in this example from the fact that higher frequencies may tend to destroy bubbles to a lesser extent than lower frequencies.

Several different means of displaying the triggered and locator frames are possible. For example, images associated with the locator frames are shown on a spatially separated region of the screen from images associated with the triggered frames. In the example, the images associated with the locator frames are shown as a small moving image situated apart from the relatively static (updated once every several cardiac cycles) triggered image.

In an alternate mode of operation, locator frames are suspended when each triggered frame is fired and for a selected period after acquisition of the triggered frame is completed. The total duration of suspension of the locator frames is 300 ms or another duration. The locator and triggered frames are displayed on the same area of the screen, so that the user sees a moving image (the locator frames) which periodically stops briefly (the triggered frames, each held for a persistence interval of 300 ms or another duration). In variations on this approach, the triggered or locator frames can be made more easily distinguishable from one another by changing their brightness or by color coding. In another variation, locator frames may be acquired during the hold period (once the triggered frame acquisition is complete), but not displayed. These frames are then available for later review.

Many alternate methods of construction are possible. For example, the locator frames may be acquired at an artificially reduced frame rate. For example, if acquisition of a frame normally takes 25 ms (40 frames/sec), the locator frames can be acquired at 100 ms intervals (10 frames/sec) by adding dead time between adjacent scan lines or frames, further decreasing bubble destruction associated with acquisition of the locator frames. Even in this case, there are preferably more locator frames than triggered frames per unit time. Also, one or both of the triggered and locator frames may be acquired using a reduced line density. Reduced line density (with subsequent loss of resolution and loss of artifact) may be acceptable for the locator frames, and can be advantageous if used with an artificially reduced frame rate so that the frame rate is not increased as the line density is reduced. In this case, the reduced line density results in a reduced level of total ultrasound energy delivered into the subject being imaged, and hence in reduced bubble destruction. Reductions in line density may be beneficial for the triggered frames, as overly high line densities may result in excessive overlap of the transmit beams, resulting in bubble destruction (one ultrasound line firing destroying bubbles which would otherwise contribute to imaging of an adjacent line).

Another alternative is that triggered frames may be acquired using fundamental imaging instead of harmonic imaging. The locator frames should be optimized to reduce degradation of the bubbles imaged in the triggered frames. The locator frames may be acquired using different transmit center frequency, bandwidth, and/or pulse shape than the triggered frames. In general, any alteration in the transmit characteristics of the locator frames which results in less destruction of the bubbles preferably imaged in the triggered frames may be advantageous. In particular, using a different transmit center frequency may result in the triggering frames selectively destroying a population of bubbles different from those primarily contributing to the triggered frame images. In some embodiments, this observation may be exploited to fullest advantage by the use of hardware or software filtering means in the transmit beamformer to remove any components at the triggered frame transmit frequency from the locator frame transmit pulses. One or both of the locator frames and triggered frames can be acquired using a chirp, swept-spectrum, coded excitation, or other high time-bandwidth product transmit pulse. Such signals may attain a given signal-to-noise ratio with lower peak pressures than a conventional ultrasound pulse, and hence may provide better performance for a given level of bubble destruction. In some implementations, such techniques may degrade image quality by worsening axial response or by worsening focusing. Such tradeoffs may be acceptable for locator frames but not for triggered frames. In the event that such transmit signals are used, the receive beamformer should include means to restore the axial resolution as well as possible.

Other transmission, receive and triggering techniques may be used, such as receiving multiple lines in a single operation based on one transmission. Preferably, ultrasonic transmissions associated with B-mode imaging are interleaved with ultrasonic transmissions associated with Doppler imaging, such as line or frame interleaving where B-mode information is used for determining perfusion and Doppler information is used for determining tissue motion. Multiple triggers may be used where each trigger is independent of each other trigger.

In another embodiment, a Doppler processor is used with a wall filter to perform pulse-to-pulse subtraction for imaging contrast agents. A first pulse acts to destroy or limit the reflectivity of contrast agents, but provides reflections from the contrast agent. A second pulse results in fewer reflections from contrast agents. The wall filter combines, such as by high pass filtering, information from the two pulses, effectively subtracting the tissue response in the two pulses. The combined information represents the contrast agents.

Using none, some or all of the transmission techniques discussed above, one or more images of tissue and contrast agent from within the heart are generated on the display 120. Since the catheter transducer 112 is within the heart, the images may provide more detail, aiding in diagnosis.

In one embodiment, the image information or information from within the image processor 118 is used to determine a quantity. For example, data generated from within the heart and reflected from contrast agents is used to determine a value or values of perfusion as discussed below. In another example, the data generated from energy reflected from contrast agents is used to determine an area or volume within the heart or other structure. A determination of volume may be aided by left ventricular opacification achieved with the contrast agent.

The volume is estimated from data representing two dimensions. Reflected energy from contrast agents within a fluid may provide a stronger indication of borders with tissue, so a blood pool area is more clearly delineated. The number of datum within a frame of data above a threshold, multiplied by an area represented by each datum, provides a measurement of area. The data included in the calculation may be limited to a user designated region of interest. Volume is estimated from the area measurement as a function of estimated volume characteristics of the blood pool or structure given the area measured. The area or volume may be measured without contrast agents. In alternative embodiments, a three-dimensional representation is generated, and the volume may be more accurately determined.

D. Diagnosis

Imaging of contrast agents and tissue with the catheter transducer 112 may assist in medical diagnosis. For example, diagnosis of heart tissue may be performed for selection of proper intervention procedures, such as balloon angioplasty, atherectomy, trans-myocardial revascularization, implanting a stent or injection of a dethrobilitic agent. Heart tissue may be diagnosed as a function of tissue movement and tissue perfusion. Tissues showing little perfusion, diskenetic movement and some perfusion, or other tissues may be aided through intervention.

High resolution images generated with the catheter transducer 112 are preferably used for diagnosis. The catheter transducer 112 is inserted into the patient in the jugular vein, femoral vein, the heart or into another portion of the vascular system of the patient. After the catheter transducer 112 is guided to a heart chamber or other portion of the vascular system for diagnosis, images are generated as discussed above.

Tissue motion, such as heart wall motion, is assessed by viewing the images or from calculations using the image data. For example, B-mode images viewed over a period of time indicate tissue motion. Likewise, Doppler processing with appropriate filtering to isolate tissue motion is used to generate images. In alternative embodiments, correlation or other techniques are used to determine a value representing the amount of tissue motion between two or more frames of data. For example, a minimum sum of absolute differences calculation is performed to estimate the amount of movement between two frames of data, such as in-phase and quadrature or B-mode data. In one alternate embodiment, tissue motion is estimated with data generated in a strip Doppler mode. Strip Doppler data is associated with a point or region within a patient and the display of a frequency spectrum along a y-axis and time along the x-axis. The strip display is preferably a gray scale display. The strength at a particular frequency modulates the brightness.

Tissue motion is preferably determined prior to injection of any contrast agent, but may be determined after injection. Contrast agents are injected as discussed above, such as into one or more of the coronary arteries (e.g., the aortic root) for perfusion estimation.

Various techniques may be used for estimating perfusion, including time intensity, triggering, absolute perfusion and binary indication. Other techniques for estimating perfusion may be used, such as visual monitoring of a plurality of Doppler or B-mode images over a period of time after injection of the contrast agent. Perfusion estimates are calculated from B-mode or intensity information instantaneously or as a function of time. Alternatively, perfusion is estimated from other data, such as in-phase and quadrature data or Doppler data.

For the binary indication technique, contrast agents are preferably injected into the patient's blood stream. The contrast agent travels to the region of interest, such as the myocardium. A greater amount of contrast agent is present in areas where perfusion is not hindered or is high, than in areas with low perfusion or blood flow. Areas with greater amounts of contrast agent are associated with higher intensities. The intensity information may be averaged as a function of time for accuracy or instantaneous values may be used. High intensity B-mode information in a region indicates high perfusion, and low intensity B-mode information indicates low perfusion. Based on the intensity level and one or more thresholds, perfusion is estimated to exist, exist at different levels or not exist.

Perfusion may also be estimated with time intensity methods, such as wash-in, wash-out or wash-in wash-out techniques. For example, contrast agents are injected. A region of interest is imaged over a time period. The change of intensity at the region of interest over the time period is measured. Various functions, such as a summation or average of intensities for a region of interest, may be used, and any region of interest may be subdivided into one or more regions of interest for separate perfusion estimation. Preferably, the ultrasound system 110 accounts for any non-linear processing (i.e., a change in intensity is not equal to a change in the amount of contrast agent). The intensity level increases as the contrast agent enters the region of interest, and the intensity decreases as the contrast agent leaves the organ. Based on the intensity level or B-mode information, the transit time of the contrast agent through the organ is calculated and is inversely related to blood flow.

Figure 9A:
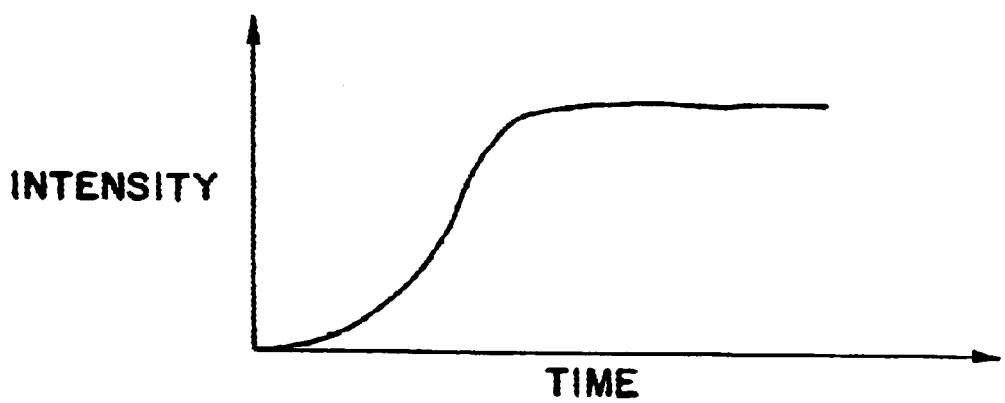
FIGS. 9A–9C are contrast agent flow curves.
Figure 9B:
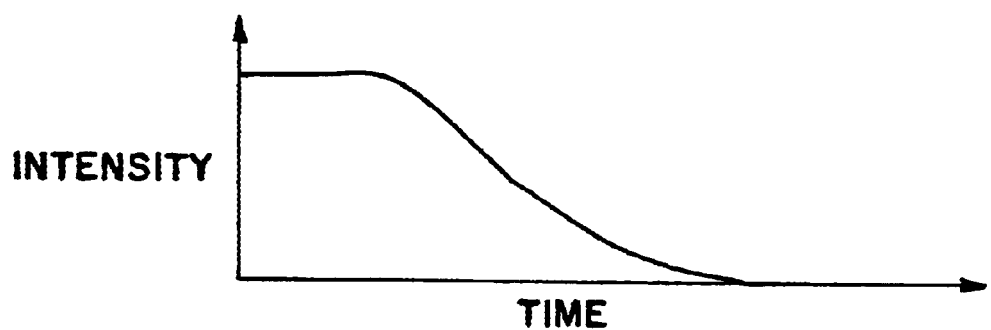
Figure 9C:
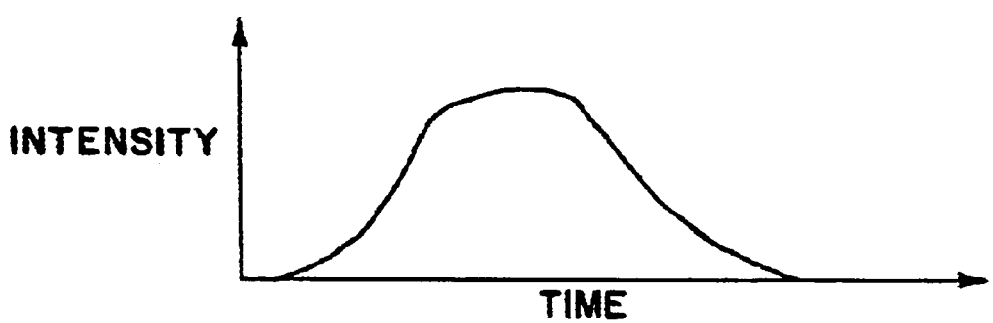

This type of time intensity estimation is a function of the time period selected. Referring to FIG. 9A, an example of a wash-in curve is represented. The curve represents an average or summed intensity as a function of the time from injection to the time to reach a peak intensity value. Referring to FIG. 9B, an intensity curve representing a wash-out curve is shown. Perfusion is estimated from the amount of time for the contrast agent to transit from a peak intensity value to a minimum value. Referring to FIG. 9C, a wash-in wash-out intensity curve is represented. Both wash-in and wash-out transit times of contrast agents are measured as discussed above. For the time intensity perfusion estimations discussed above, various time periods as a function of intensity may be measured, such as times from or to intensities at a percentage above or below the peak and minimum intensity values. Preferably, any percentages are determined through experimentation, and may be about 10 to 20 percent of the peak and minimum intensity values. Furthermore, either continuous or triggered imaging may be used for time intensity calculations.

Perfusion may be estimated using triggering. For example, a triggering rate is varied. Preferably, high power ultrasonic waves are transmitted at each trigger and the intensity of the echoes is measured. Based on the resulting destruction of the contrast agent, the triggering rate is adjusted to maintain a steady state intensity. If the triggering rate or time between triggers is long, intensity increases. If the triggering rate is too rapid, the intensity decreases due to contrast agent destruction. The rate of triggering (i.e. the time period between triggered frames) associated with a steady state intensity estimates perfusion. In alternative embodiments, the rate of triggering is not altered. An average intensity is determined as a function of each triggered frame of data. Perfusion is estimated as a function of the trigger rate and the average intensity.

Perfusion may be estimated using absolute perfusion calculations, such as described in U.S. application Ser. No. 08/949,237 for AN ULTRASONIC METHOD AND SYSTEM FOR MEASURING PERFUSION, filed Oct. 10, 1997, the disclosure of which is herein incorporated by reference. For absolute perfusion, contrast agent is constantly infused with an infusion pump. Preferably, Doppler imaging is associated with lower power transmission. After a constant intensity at the region of interest is established, a high powered ultrasonic wave is transmitted to destroy the contrast agent. Either triggers or the user activate transmission of the high power ultrasonic wave. The increase in intensity after transmission of the high power ultrasonic wave is used to estimate perfusion. In a preferred embodiment, the absolute measure of perfusion is determined from the equation: $\ln[c(t\alpha)-c(t)]=\ln[c(t\alpha)-c(t_0)]-(f/V)t$, where $c(t\alpha)$ is the concentration of contrast agent at infinity (i.e. a steady state value), $c(t)$ is the concentration of contrast at time t, f is the true blood flow rate and V is the volume fraction of blood within the region of interest. Preferably, the concentration is a measure of the intensity at a point in the processing paths where signals are linear. The fraction f/V is the absolute measure of flow per unit volume. Other equations may be used.

Preferably, imaging for determining perfusion is finished over a period of three or four heart cycles. If a larger interval of time is used, new areas of the heart may enter any user specified region of interest and may adversely affect perfusion estimation. Furthermore, other methods of perfusion estimation may be used.

Imaging with the catheter transducer 112 in the heart provides images of the myocardium without interference from the lungs, ribs or even other tissue layers. Many cardiac structures may be more uniformly imaged from within the heart than from outside the heart. Injecting and imaging contrast agents with the catheter transducer 112 may allow for more accurate diagnosis, such as by providing accurate perfusion estimation. Through selective injection into one or more of the major coronary arteries, perfusion is observed from images with minimized interference. Using accurate perfusion information and/or tissue information, the catheter transducer may be used to guide any intervention.

While the invention has been described above by reference to various embodiments, it will be understood that many changes and modifications can be made without departing from the scope of the invention. For example, different imaging modes, transmission techniques, reception frequencies, or diagnostic procedures may be used.

It is therefore intended that the foregoing detailed description be understood as an illustration of the presently preferred embodiments of the invention, and not as a definition of the invention. It is only the following claims, including all equivalents, that are intended to define the scope of this invention.

What is claimed is:

1. A method for generating contrast images from within a body with an ultrasound system, the method comprising the steps of:
    (a) transmitting ultrasonic acoustic energy from a catheter transducer;
    (b) receiving reflected energy responsive to step (a) and contrast agents without interference from intervening structures with the catheter transducer; and
    (c) generating an image responsive to the reflected energy.

2. The method of claim 1 further comprising step (d) obtaining information at a harmonic of the transmitted ultrasonic acoustic energy from the reflected energy;
    wherein the image is responsive to the information at the harmonic.

3. The method of claim 1 further comprising step (d) estimating perfusion as a function of the reflected energy.

4. The method of claim 3 wherein step (d) comprises calculating a contrast agent transit time as a function of the reflected energy.

5. The method of claim 3 wherein step (d) comprises:
    (d1) substantially destroying contrast agents; and
    (d2) calculating perfusion as a function of the reflected energy and time.

6. The method of claim 3 wherein step (d) comprises:
    (d1) repeating step (a);
    (d2) triggering step (d1) at a trigger rate;
    (d3) adjusting the trigger rate in response to the reflected energy; and
    (d4) calculating perfusion as a function of the triggering rate.

7. The method of claim 3 wherein step (d) comprises estimating the perfusion as an absolute perfusion calculation.

8. The method of claim 3 wherein step (d) comprises estimating the perfusion as a calculation selected from the group consisting of: wash-in, washout and wash-in wash-out.

9. The method of claim 3 wherein step (d) comprises estimating the perfusion as a function of a triggering rate.

10. The method of claim 1:
    further comprising repeating steps (a), (b) and (c); and
    wherein at least one repetition of step (a) is associated with a first power level of the ultrasonic acoustic energy and at least another repetition of step (a) is associated with a second power level that is less than the first power level.

11. The method of claim 1 further comprising step (d) determining an area value responsive to the reflected energy.

12. The method of claim 1:
    further comprising repeating steps (a) and (b), at least one transmission of ultrasonic acoustic energy responsive to a first phase and at least another transmission of ultrasonic acoustic energy responsive to a second phase that is shifted from the first phase;
    further comprising step (d) combining reflected energy responsive to the first phase with reflective energy responsive to the second phase;
    wherein the image is responsive to step (d).

13. The method of claim 1 further comprising step (d) detecting tissue motion.

14. The method of claim 13 wherein step (d) comprises a process selected from the group of: (i) Doppler processing (ii) correlation processing, (iii) image display processing as a function of time and (iv) combinations thereof.

15. The method of claim 13 further comprising (e) injecting contrast agents after step (d).

16. The method of claim 15 further comprising step (f) estimating perfusion as a function of the reflected energy after step (e).

17. The method of claim 1 wherein step (a) comprises transmitting the ultrasonic acoustic energy from a plurality of elements, each of the plurality of elements spaced at least one wavelength from other ones of the plurality of elements.

18. The method of claim 1 wherein step (a) comprises transmitting from a transducer selected from the group consisting of intra-vascular and intra-cardiac.

19. The method of claim 1 wherein step (c) comprises processing selected from the group consisting of: applying a wall filter to detect contrast agents, triggering to detect contrast agents and combinations thereof.

20. The method of claim 1 wherein step (a) comprises transmitting from a linear array of elements.

21. An ultrasound system dapted for generating contrast images from within a body without interference from intervening structures, the system comprising:
    a catheter transducer for transmitting ultrasonic acoustic energy and for receiving reflected energy responsive to the transmitted ultrasonic acoustic energy and contrast agents without interference from intervening structures; and
    an image processor for generating an image responsive to the reflected energy.

22. The system of claim 21 wherein the image processor is operable to obtain information at a harmonic of the transmitted ultrasonic acoustic energy from the reflected energy and the image is responsive to the information at the harmonic.

23. The system of claim 21 further comprising an estimate of perfusion responsive to the reflected energy.

24. The system of claim 21 further comprising a means for triggering transmission of the ultrasonic acoustic energy.

25. The system of claim 21 further comprising:
    a beamformer operatively connected between the catheter transducer and the image processor; and
    a beamformer controller operative to cause a first transmission of the ultrasonic acoustic energy at a first power level and to cause a second transmission of the ultrasonic acoustic energy at a second power level that is less than the first power level.

26. The system of claim 21 further comprising an estimate of an area responsive to the reflected energy.

27. The system of claim 21 further comprising:
    a beamformer operatively connected between the catheter transducer and the image processor;
    a beamformer controller operative to cause a first transmission of the ultrasonic acoustic energy at a first phase and to cause a second transmission of the ultrasonic acoustic energy at a second phase that is shifted from the first phase;
    wherein the image processor is operable to combine reflected energy responsive to the first phase with reflective energy responsive to the second phase; and
    wherein the image is responsive to the result of the combination.

28. The system of claim 21 wherein the image processor comprises a Doppler processor for generating tissue motion information.

29. The system of claim 21 wherein the catheter transducer comprises a plurality of elements, each of the plurality of elements spaced at least one wavelength from other ones of the plurality of elements.

30. The system of claim 21 wherein the catheter transducer comprises a transducer selected from the group consisting of: intra-vascular and intra-cardiac.

31. The system of claim 21 wherein the image processor comprises a Doppler processor and wall filter.

32. The system of claim 21 wherein the catheter transducer comprises a linear array of elements.

33. A method for generating contrast images from within a body with an ultrasound system, the method comprising the steps of:
   (a) transmitting ultrasonic acoustic energy from a catheter transducer comprising a linear array of elements;
   (b) receiving reflected energy responsive to step (a) and contrast agents with the catheter transducer; and
   (c) generating an image responsive to the reflected energy.

34. The method of claim 33 further comprising step (d) obtaining information at a second harmonic of the transmitted ultrasonic acoustic energy from the reflected energy;
   wherein the image is responsive to the information at the second harmonic.

35. The method of claim 33 further comprising step (d) estimating perfusion as a function of the reflected energy.

36. The method of claim 33:
   further comprising repeating steps (a), (b) and (c); and
   wherein at least one repetition of step (a) is associated with a first power level of the ultrasonic acoustic energy and at least another repetition of step (a) is associated with a second power level that is less than the first power level.

37. The method of claim 33 further comprising step (d) determining an area value responsive to the reflected energy.

38. The method of claim 33:
   further comprising repeating steps (a) and (b), at least one transmission of ultrasonic acoustic energy responsive to a first phase and at least another transmission of ultrasonic acoustic energy responsive to a second phase that is shifted from the first phase;
   further comprising step (d) combining reflected energy responsive to the first phase with reflective energy responsive to the second phase;
   wherein the image is responsive to step (d).

39. The method of claim 33 further comprising step (d) detecting tissue motion.

40. The method of claim 33 wherein step (a) comprises transmitting the ultrasonic acoustic energy from a plurality of elements, each of the plurality of elements spaced at least one wavelength from other ones of the plurality of elements.

41. The method of claim 33 wherein step (a) comprises transmitting from a transducer selected from the group consisting of intra-vascular and intra-cardiac.

42. The method of claim 33 where step (c) comprises processing selected from the group consisting of: applying a wall filter to detect contrast agents, triggering to detect contrast agents and combinations thereof.

43. An ultrasound system for generating contrast images from within a body, the system comprising:
   a catheter transducer comprising a linear array of elements for transmitting ultrasonic acoustic energy and for receiving reflected energy responsive to the transmitted ultrasonic acoustic energy and contrast agents; and
   an image processor for generating an image responsive to the reflected energy.

44. The system of claim 43 wherein the image processor is operable to obtain information at a harmonic of the transmitted ultrasonic acoustic energy from the reflected energy and the image is responsive to the information at the harmonic.

45. The system of claim 43 further comprising an estimate of perfusion responsive to the reflected energy.

46. The system of claim 43 further comprising a means for triggering transmission of the ultrasonic acoustic energy.

47. The system of claim 43 further comprising:
   a beamformer operatively connected between the catheter transducer and the image processor; and
   a beamformer controller operative to cause a first transmission of the ultrasonic acoustic energy at a first power level and to cause a second transmission of the ultrasonic acoustic energy at a second power level that is less than the first power level.

48. The system of claim 43 further comprising an estimate of an area responsive to the reflected energy.

49. The system of claim 43 further comprising:
   a beamformer operatively connected between the catheter transducer and the image processor;
   a beamformer controller operative to cause a first transmission of the ultrasonic acoustic energy at a first phase and to cause a second transmission of the ultrasonic acoustic energy at a second phase that is shifted from the first phase;
   wherein the image processor is operable to combine reflected energy responsive to the first phase with reflective energy responsive to the second phase; and
   wherein the image is responsive to the result of the combination.

50. The system of claim 43 wherein the image processor comprises a Doppler processor for generating tissue motion information.

51. The system of claim 43 wherein the catheter transducer comprises a plurality of elements, each of the plurality of elements spaced at least one wavelength from other ones of the plurality of elements.

52. The system of claim 43 wherein the catheter transducer comprises a transducer selected from the group consisting of: intra-vascular and intra-cardiac.

53. The system of claim 43 where the image processor comprises a Doppler processor and wall filter.

* * * * *